United States Patent [19]

Small

[11] Patent Number: 5,898,002
[45] Date of Patent: Apr. 27, 1999

[54] METHOD FOR REMOVING FERRIC-FERROUS OXIDES FROM A LIQUID

[75] Inventor: Terence P. Small, Aldan, Pa.

[73] Assignee: BetzDearborn Inc., Trevose, Pa.

[21] Appl. No.: 08/916,198

[22] Filed: Aug. 22, 1997

[51] Int. Cl.[6] .................................................. G01N 21/79
[52] U.S. Cl. .................................. 436/6; 436/84; 436/175
[58] Field of Search ...................................... 210/695, 222; 436/6, 84, 175

[56] References Cited

U.S. PATENT DOCUMENTS

| | | | |
|---|---|---|---|
| 3,836,331 | 9/1974 | Stookey | 23/230 R |
| 3,887,457 | 6/1975 | Marston et al. | 210/222 |
| 3,934,192 | 1/1976 | De Latour | 436/84 |
| 4,529,517 | 7/1985 | Bertil | 210/223 |
| 4,806,264 | 2/1989 | Murphy | 210/695 |
| 5,236,845 | 8/1993 | Pierce et al. | 436/6 |

FOREIGN PATENT DOCUMENTS

| | | |
|---|---|---|
| 0 469 772 A2 | 6/1992 | European Pat. Off. . |
| 0 469 773 B1 | 9/1996 | European Pat. Off. . |

OTHER PUBLICATIONS

T.–Y. Chen, M.R. Godfrey and S.C. Avollone, "Corrossion and Corrosion Product Transport Monitoring in Boiler Condensate Systems", Paper No. 336, Corrossion 94, The Annual Conference and Corrosion Show Sponsored by NACE International, pp. 1–18.

"Interactions of Metal Hydrous Oxides with Chelating Agents. Part V. Magnetite–EDTA", Han–Chyen Chang and Egon Matijevic, Finn. Chem. Lett. 1982, pp. 90–95.

"The Kinetics of the Schikorr Reaction on Steel Surfaces at Low Temperatures", S.L. Webb and G. Bohnsack, Paper 311, Corrosion 89, pp. 1–8, 1989.

M.R. Godfrey, T.–Y. Chen, and I.E. Eisner,"On–line Corrosion Monitoring In Boiler Systems", *Corrosion*/95, paper No. 621.

L.L. Stookey, "Ferrozine–A New Spectrophotometric Reagent for Iron", *Analytical Chemistry*, vol. 42, No. 7, pp. 779–781, 1970.

G. Bohnsak, The solubility of magnetite in water and in aqueous solutions of acid and alkali, chapter 5, pp. 72–89, Vulkan–Verlag, Essen, 1987.

"Characterization and Application of FerroZine Iron Reagent as a Ferrous Iron Indicator", C.R. Gibbs, *Analytical Chemistry*, 48(8), pp. 1197–1201, 1976.

M.R. Godfrey and T.–Y. Chen, "Monitoring Corrosion in Boiler Systems with Colorimetric Tests for Ferrous and Total Iron", *Corrosion*, vol. 51, No. 10. pp. 797–804.

*Primary Examiner*—Jeffrey Snay
*Attorney, Agent, or Firm*—Matthew W. Smith

[57] ABSTRACT

A method for removing ferric-ferrous oxides from a liquid containing ferric-ferrous oxides and ferrous ions and to a method for determining the amount of ferrous ion in a liquid. The invention has particular utility for use in a method to accurately determine the corrosion rates of ferrometals in contact with aqueous liquids by filtering ferric-ferrous oxides from the aqueous liquid prior to determining the ferrous ion content of the aqueous liquid.

4 Claims, 2 Drawing Sheets

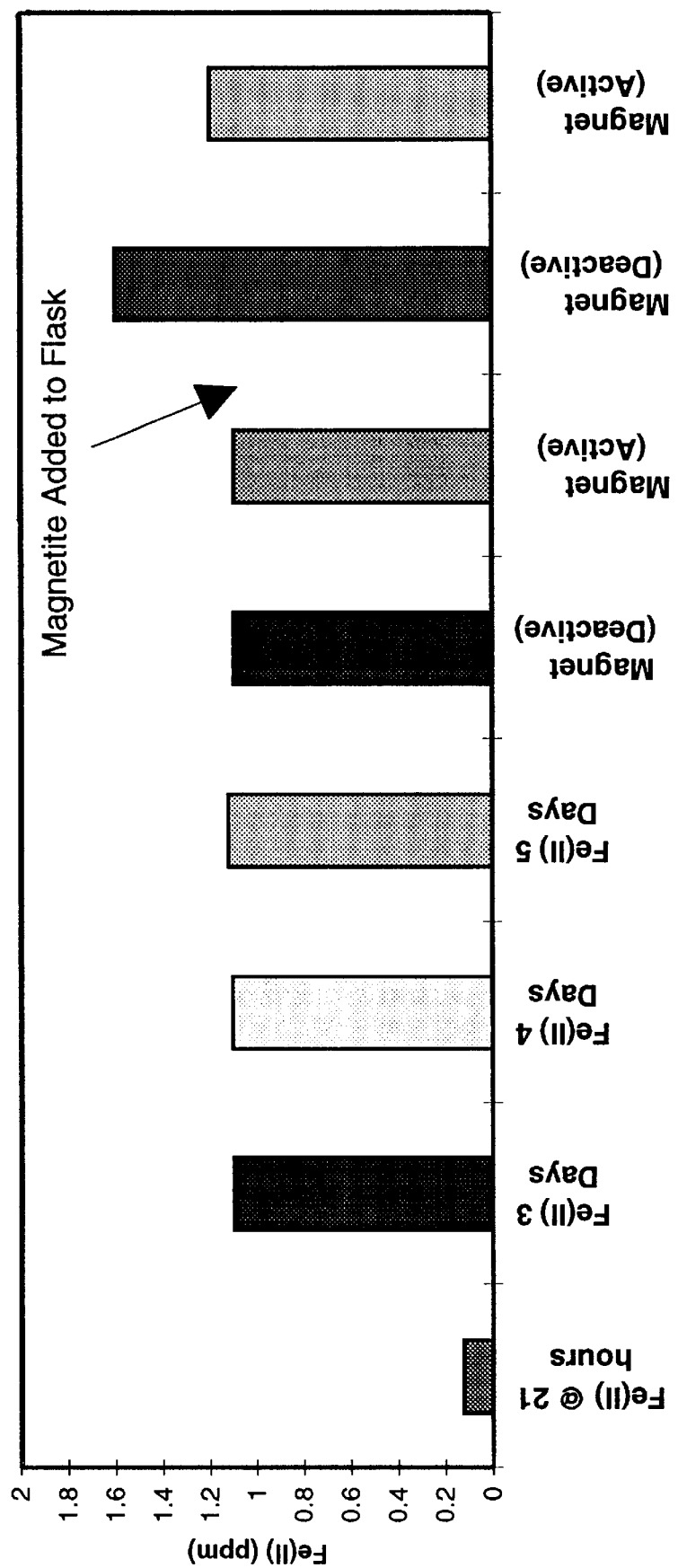

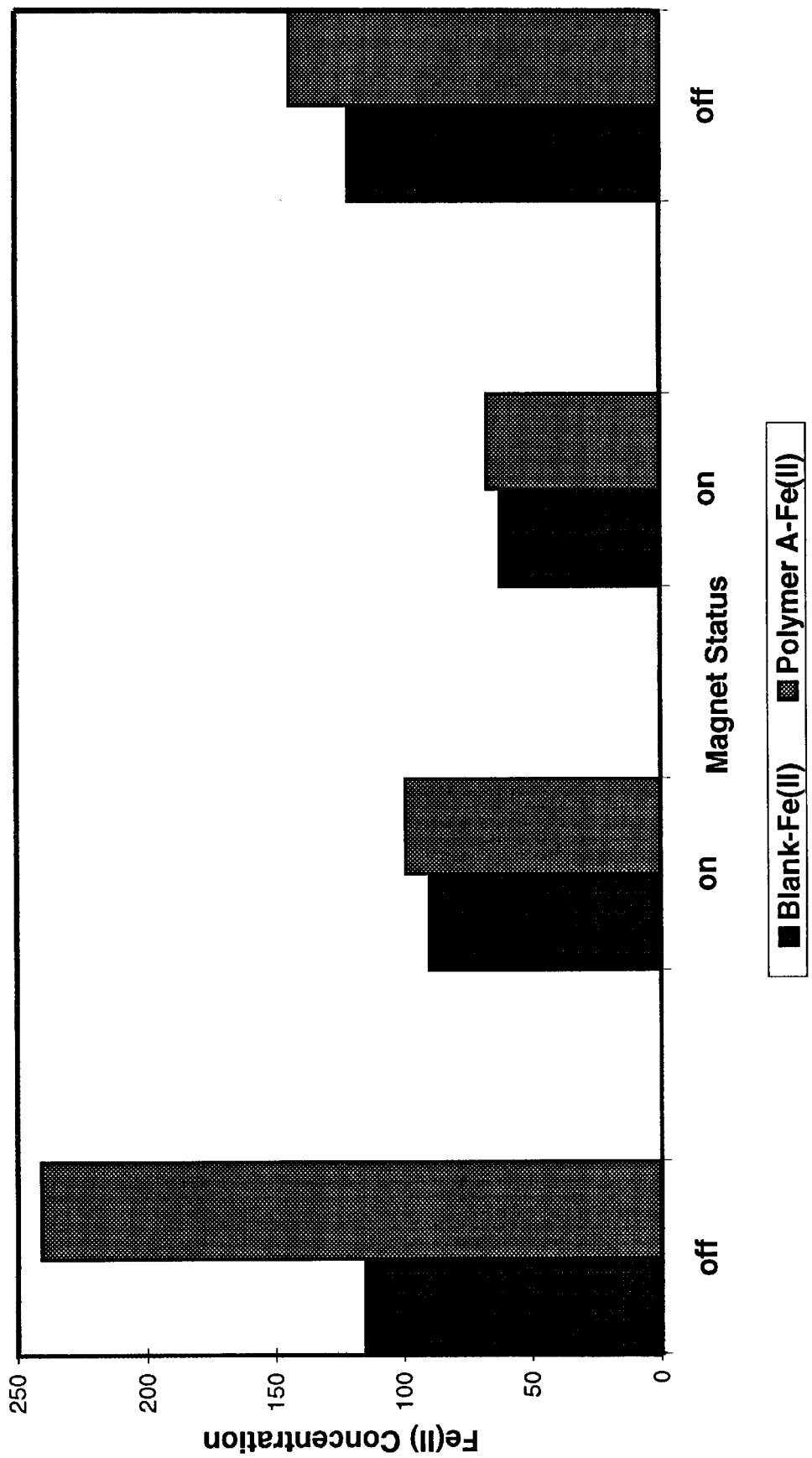

METHOD FOR REMOVING FERRIC-FERROUS OXIDES FROM A LIQUID

FIELD OF THE INVENTION

The present invention relates to a method for removing ferric-ferrous oxides from a liquid containing ferric-ferrous oxides and ferrous ions and to a method for determining the amount of ferrous ion in a liquid. More particularly, the present invention relates to a method for accurately determining the corrosion rates of ferrometals in contact with aqueous liquids by filtering ferric-ferrous oxides from the aqueous liquid prior to determining the ferrous ion content of the aqueous liquid.

BACKGROUND OF THE INVENTION

Corrosion is generally a problem in any system in which ferrous metals are in contact with aqueous solutions. Corrosion is the electrochemical reaction of metal with its environment. Corrosion is a destructive reaction which, simply stated, is the reversion of refined metals to their natural state. For example, iron ore is iron oxide. Iron oxide is refined into steel. When the steel corrodes, it forms iron oxide.

The metallurgy of boiler systems are predominantly iron-containing steel in contact with high temperature (approximately 200° F., under 35–350 psig of pressure) aqueous solutions. Most industrial boiler and feedwater systems are constructed of carbon steel and sometimes with copper alloy and/or stainless steel feedwater heaters and condensers. Some have stainless steel super-heater elements.

Corrosion is one of the main causes of reduced reliability in boiler systems. The most common causes of corrosion are dissolved gases such as carbon dioxide and oxygen, under-deposit attack, low pH and attack of areas weakened by mechanical stress resulting in stress and fatigue cracking. Corrosion control in boilers varies with the type of corrosion encountered. Generally, corrosion in boilers may be controlled through procedures such as maintaining proper pH and alkalinity levels, reducing mechanical stresses, operating within design temperature and pressure specifications, by proper application of chemical corrosion inhibiting treatments and by controlling oxygen and boiler feedwater contamination. Generally boiler feedwater should be low in contaminants. The American Society of Mechanical Engineers (ASME) Consensus for Industrial Boilers specifies maximum levels of contaminants for corrosion and deposition control in boiler systems. The consensus is that feedwater oxygen, iron and copper content should be less than 7 parts per billion (ppb) oxygen, 20 ppb iron and 15 ppb copper for a 900 psig boiler and that pH should be maintained between 8.5 and 9.5 for boiler system corrosion protection.

It is commonly held that in boiler systems substantially free of oxygen (i.e., less than about 7 ppb oxygen) that ferrometal corrosion can be expressed in terms of the following equation:

$$Fe + 2H_2O \rightarrow Fe(OH)_2 + H_2.$$

Therefore, $Fe^{+2}$ (ferrous ion) is a useful material to determine the corrosion rate of ferrometals in substantially oxygen free systems such as boilers. However, in the presence of oxygen the following reaction occurs:

$$3Fe(OH)_2 \rightarrow Fe_3O_4 + H_2 + 2H_2O$$

Magnetite ($Fe_3O_4$) is a complex of the hydroxides of iron (III) and iron (II) which can be expressed by the formula:

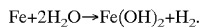

Other ferric-ferrous oxide species also exist, however, under the conditions present in most boiler water, magnetite is the most common species. As used herein the term "ferric-ferrous oxide" means magnetite as well as other ferric-ferrous oxide species such as maghemite ($\gamma Fe_2O_3$) and feroxyhyte ($\delta FeOOH$) which are ferrimagnetic. Ferric-ferrous oxides are often introduced into a boiler system by boiler feedwater. Ferric-ferrous oxides can also be produced within the boiler through reaction of ferrous ions with trace free oxygen and via electrochemical reactions.

Ferrion chelation chemicals are compounds which form complex undissociated cations with divalent metal ions. Such chelation chemicals include 1,10-phenanthrolinre; 4,7-diphenyl-1,10-phenanthroline; $2,2_1$bipyridine; 2,6-bis(2-pyridyl)-pyridine; 2,4,6-(bis(2-pyridyl)-1,3,5-triazine; phenyl 2-pyridyl ketoxime; 3-(2-pyridyl)-5,6-bis(4-phenylsulfonic acid)-1,2,4-nitrilotriacetic acid and salts thereof. Certain of these ferrion chelation chemicals react with ferrous ions to form colored species (ferroin reagents) which are useful in the coloromertric determination of ferrous ion concentration. It is generally believed that ferroin reagents do not change color when the reagent complexes with ferric ($Fe^{+3}$) ions in water. However, some research suggests that oxides, such as magnetite, may be captured by the ferroin reagents and thus bias ferrous ion content determinations (see Matijevic, E. Han-Chyen, Chang, *Interactions of Metal Hydrous Oxides with Chelating Agents: Part V Ferric-ferrous oxides-EDTA*, J. Colloid Interface Sci., Fin. Chem. Lett. (1982); and Bohnsak, G. *The Solubility of Ferric-ferrous oxides in Water and in Aqueous Solutions of Acid and Alkali* (Essen: Vielkan-Verlag, 1987)).

Therefore, conventional techniques to measure ferrous ion content as an indicator of ferrous metal corrosion may inadvertently include some ferric-ferrous oxides concentration in the calculation of ferrous ion thereby yielding higher corrosion rate determinations then are actually occurring in the studied boiler system.

Thus a need exists for a method to remove ferric-ferrous oxides from a liquid containing ferric-ferrous oxides and ferrous ions.

A need also exists for a method to measure the ferrous ion concentration in boiler water without contamination of the rate determination results due to the presence of ferric-ferrous oxides in the boiler water.

It is, therefore, an object of this invention to provide a method for removing ferric-ferrous oxides from a liquid containing ferric-ferrous oxides and ferrous ions.

It is also an object of this invention to provide an accurate method to determine the corrosion rate of ferrous metals exposed to a boiler water in a boiler system which contains ferrous ions, ferric ions and/or ferric-ferrous oxides.

PRIOR ART

U.S. Pat. No. 5,236,845 to Pierce et al. discloses a method for determining the presence of ferrous ion in boiler water. The method can be used to measure the rate of corrosion in the boiler water. The method uses a complex formed between ferrous ion and 3-(2-pyridyl)-5,6-diphenyl-1,2,4-triazine-p,p'-disulfonic acid monohydrate reagent and spectophotometric analysis to determine corrosion rates in a boiler system.

U.S. Pat. No. 3,836,331 to Stookey discloses 3-(2-pyridyl)-5,6-bis(phenylsulfonic acid)-1,2,4-triazine and certain salts thereof are useful as reagents in the spectrophotometric determination of iron in water or other solutions.

European Patent Application No. 469772A2 discloses an on-line analyzer for the determination of low level ferrous ion in an aqueous solution such as found in boiler systems.

BRIEF DESCRIPTION OF THE DRAWINGS

The appended drawings graphically present the data generated by the examples which are reported herein below. In the drawings:

FIG. 1 is a graph of Fe(II) concentration versus time; and

FIG. 2 is a graph of Fe(II) concentration versus magnet status.

SUMMARY OF THE INVENTION

To achieve the foregoing and other objects, the present invention provides a method of separating ferric-ferrous oxides from a liquid solution containing ferric-ferrous oxides and ferrous ions. The method comprises the steps of:

(a) exposing a liquid solution containing ferric-ferrous oxides and ferrous ions to a magnetic field to capture said ferric-ferrous oxides; and (b) removing said liquid containing said ferrous ion from said magnetic field.

The present invention also provides a method of determining corrosion rates of ferrometals in contact with an aqueous system. The method comprises:

(a) placing an aqueous liquid containing ferric-ferrous oxides and dissolved ferrous ions, into a magnetic field to magnetically filter said ferric-ferrous oxides from said aqueous liquid;

(b) obtaining a known aliquot volume sample of said magnetically filtered liquid of step (a);

(c) adding said sample of step (b) to a known volume of spectrophotometric reagent solution;

(d) mixing said sample and said reagent solution of step (c) to form a ferrous ion/reagent complex solution;

(e) generating a standard ferrous ion/reagent complex absorption curve at a predetermined wavelength for standards containing known amounts of ferrous ion and reagent;

(f) measuring spectrophotometricaliy the absorption of the ferrous ion/reagent solution of step (d) at said predetermined wavelength of step (e);

(g) calculating the amount of ferrous ion present by comparing the absorption of ferrous ion/reagent complex solution of step (f) with said standard curve of step (e); and (h) repeating steps (a)–(g) to determine an actual corrosion rate.

DETAILED DESCRIPTION OF THE INVENTION

The present inventor has discovered that ferric-ferrous oxides can be effectively filtered from a liquid sample containing ferric-ferrous oxides and ferrous ions by use of a magnetic field. This discovery has particular usefulness in the removal of ferric-ferrcous oxides from samples of boiler water in order to accurately determine the ferrous ion content of the sample, and to determine the corrosion rate of ferrometals exposed to the boiler water in a boiler water system.

The inventor has discovered that by subjecting a portion of boiler water containing ferric-ferrous oxides and ferrous ions, in a substantially oxygen free environment, to a magnetic current, that the ferrimagnetic ferric-ferrous oxides tend to remain within the magnetic field while the water and the paramagnetic ferrous ion can be removed from the magnetic field, thereby allowing the water containing the ferrous ions to be separated from the ferric-ferrous oxides.

This discovery is useful in a method of determining corrosion rates of ferrometals in contact with an aqueous system and has particular utility for determining ferrometal corrosion rate in boilers. The method comprises:

(a) placing an aqueous liquid containing ferric-ferrous oxides and dissolved ferrous ions, into a magnetic field to magnetically filter said ferric-ferrous oxides from said aqueous liquid;

(b) obtaining a known aliquot volume sample of said magnetically filtered liquid of step (a);

(c) adding said sample of step (b) to a known volume of spectrophotometric reagent solution;

(d) mixing said sample and said reagent solution of step (c) to form a ferrous ion/reagent complex solution;

(e) generating a standard ferrous ion/reagent complex absorption curve at a predetermined wavelength for standards containing known amounts of ferrous ion and reagent; (f) measuring spectrophotornetric ally the absorption of the ferrous ion/reagent solution of step (d) at said predetermined wavelength of step (e);

(g) calculating the amount of ferrous ion present by comparing the absorption of ferrous ion/reagent complex solution of step (f) with said standard curve of step (e); and (h) repeating steps (a)–(g) to determine an actual corrosion rate.

The spectophotometric reagent can be any suitable ferrion chelation chemical which forms colored, complex undissociated cations with divalent metal ions. The preferred spectophotometric reagents are 1,10-phenanthroline; 4,7-diphenyl-1,10-phenanthroline; 2,2$^1$bipyridine; 2,6-bis(2-pyridyl)-pyridine; 2,4,6-(bis(2-pyridyl)-1,3,5-triazine; phenyl 2-pyridyl ketoxime and salts thereof. The most preferred reagent is 3-(2-pyridyl)-5,6-bis(4-phenylsulfonic acid)-1,2,4-nitrilotriacetic acid and salts thereof.

Any spectophotometric technique to determine Fe(II) concentration in a liquid sample can be used in the method of this invention. The preferred spectophotometric techniques are those utilizing a Hach DR 2000 spectrophotometer.

This invention can also be used in on-line chemical analysis systems or in analytical methods utilizing grab sampling techniques.

The present invention is described further with reference to the following specific examples which are to be regarded solely as illustrative and not restricting the scope of the invention.

EXAMPLE I

Ten grams of 1040 steel screen was washed with HCl and rinsed with water and placed in a glass reaction vessel to provide an iron (II) source. A solution of deionized water buffered with trisodium phosphate to a pH of 10.7 was placed in the glass reaction vessel with the steel screen. The buffered water was then sparged with nitrogen to remove oxygen and provide agitation. The reaction vessel temperature was maintained at 50° C. throughout the test. The reaction vessel was equipped with a glass pipette that extended from the solution to a glass cooling condenser. The condenser was attached to a syringe containing oxygen free Ferrozine reagent. Samples of the aqueous solution containing Iron (II) were extracted from the flask and analyzed once per day for five days. Samples were analyzed with a Hach DR 2000 spectrophotometer using a Ferrozine reagent. Analyses of the samples yielded an equilibrated Fe(II) concentration of 1.1 ppm. On the final day of the test, a magnet was held close to the reaction vessel and a sample of liquid was withdrawn. The sample yielded an equilibrated Fe(II) concentration of 1.1 ppm, indicating that ferrous ions are not retained in a magnetic field.

The magnet was deactivated and magnetite particles were added to the reaction vessel. Prior to the addition of magnetite, the ferrous ion solution appeared to be clear. After the addition of magnetite, the magnetite-ferrous ion solution appeared to be translucent black. A sample was withdrawn from the reaction vessel and analyzed for ferrous iron content. The analyses yielded an Fe(II) concentration of 1.6 ppm. The magnetic field was reintroduced near the reaction vessel and the magnetite particles appeared to be retained along the side of the reaction vessel exposed to the magnetic field. The solution also appeared to clear. A sample was withdrawn from the reaction vessel and yielded a ferrous ion concentration of 1.2 ppm.

The results are shown in FIG. 1.

EXAMPLE II

Simulated boiler water solutions containing ferrous ion and ferric-ferrous oxides were prepared by growing magnetite particles from a soluble iron (II) amine complex in a pH 10.3 phosphate buffered solution which contained less than about 50 ppb oxygen. The amine binds to the ferrous ion sites at room temperature and decomposes upon heating, releasing Fe(II), which simulates the Fe(II) released from a steel surface during operation of a boiler. The low oxygen concentration reacts with some Fe(II) to form Fe(III). The Fe(II), Fe(III), and remaining oxygen provide the proper conditions for magnetite particle formation. Without a dispersant, the magnetite particle size averaged 5 um. The particle size of the magnetite was modified by adding various concentrations of a boiler dispersant, poly-(isopropenylphosphonic acid)(PIPPA). When 75 ppm of PIPPA was added to the autoclave charge solution, the particle size was reduced to 0.2 um.

Samples of the simulated boiler water solutions were placed in an oxygen free reaction vessel, and heated to 280° C. at 1000 psig with constant stirring. A sample was withdrawn and dispensed through a shell and tube heat exchanger. The cooled sample was dispensed through a septum with the assistance of a syringe into nitrogen purged vials containing Ferrozine reagent.

An electromagnet was positioned between the heat exchanger and the Ferrozine reagent and the vials containing Ferrozine solution to provide a magnetic current to certain samples.

The results are shown in FIG. II.

FIG. II shows that the magnetic field applied to the samples removed magnetite as indicated by the decrease in iron (II) concentration in the samples which were exposed to the magnetic current. FIG. II also indicates that Ferrozine reacted colorcmetrically with magnetite in Example II.

Thus, the present invention provides a method of separating ferric-ferrous oxides from a liquid solution containing ferric-ferrous oxides and ferrous ions.

The invention also provides a method of determining corrosion rates in ferrometals in contact with an aqueous solution, which allows ferrometal corrosion rate determinations to be calculated without the interference from ferric-ferrous oxides.

While this invention has been described with respect to particular embodiments thereof, it is apparent that numerous other forms and modifications of the invention will be obvious to the skilled artisan. The appended claims and this invention generally should be construed to cover all such obvious forms and modifications which are within the true spirit and scope of the present invention.

I claim:

1. A method of determining corrosion rates of ferrometals in contact with an aqueous system, said method comprising:
   (a) placing an aqueous; liquid containing ferric-ferrous oxides and dissolved ferrous ions, into a magnetic field to magnetically filter said ferric-ferrous oxides from said aqueous liquid;
   (b) obtaining a known aliquot volume sample of said magnetically filtered liquid of step (a);
   (c) adding said sample of step (b) to a known volume of spectrophotometric reagent solution;
   (d) mixing said sample and said reagent solution of step (c) to form a ferrous ion/reagent complex solution;
   (e) generating a standard ferrous ion/reagent complex absorption curve at a predetermined wave length for standards containing known amounts of ferrous ion and reagent;
   (f) measuring spectrophotometrically the absorption of the ferrous ion/reagent solution of step (d) at said predetermined wave length of step (e);
   (g) calculating the amount of ferrous ion present by comparing the absorption of ferrous ion/reagent complex solution of step (f) with said standard curve of step (e); and
   (h) repeating steps (a)–(g) to determine an actual corrosion rate.

2. The method of claim 1 wherein said reagent is selected from the group consisting of 1,10-phenanthroline; 4,7-diphenyl-1,10phenanthroline; 2,2$^1$bipyridine; 2,6-bis(,2-pyridyl)-pyridine; 2,4,6-(bis(2pyridyl)-1,3,5-triazine; phenyl 2-pyridyl ketoxime; 3-(2-pyridyl)-5,6-bis(4-phenylsulfonic acid)-1,2,4-nitrilotriacetic acid and salts thereof.

3. On a method of determining actual corrosion rates of boiler system ferrometals in contact with boiler system water containing boiler water treatment chemicals, which method comprises the steps of:
   obtaining a known aliquot volume of a boiler water sample;
   adding the known volume of the sample to a known volume of an acidic buffer solution, buffered at a pH of from 2.0 to 6.0, the acidic buffer solution including an effective concentration of 3-(2pyridyl)-5,6-diphenyl-1,2,4-triazine-p,p'-disulfonic acid monosodium salt monohydrate reagent, wherein no reducing agents are added prior to the step of adding the known volume of the acidic buffer solution;
   mixing the sample and acidic buffer solution to form a soluble ferrous ion/3-(2-pyridyl)-5,6-diphenyl-1,2,4-triazine-p,p'-disulfonic acid complex solution;
   generating a standard ferrous ion/3-(2-pyridyl)-5,6-diphenyl-1,2,4-triazine-p,p'-disulfonic acid absorption curve for a standard solution containing a known value of 3-(2-pyridyl)-5,6-diphenyl-1,2,4-triazine-p,p'-disulfonic acid;
   measuring spectrophotometrically the absorption of the ferrous ion/3-(2-pyridyl-5,6-diphenyl-1,2,4-triazine-p,p'-disulfonic acid complex solution at a wavelength of about 560±30 manometers;
   calculating the amount of ferrous ion present by comparing the absorption of the ferrous ion/3-(2-pyridyl)-5,6-diphenyl-1,2,4-triazine-p,p'-disulfonic complex solution acid to the standard absorption curve; and
   repeating the steps of obtaining, adding, mixing, generating, measuring and calculating so as to determine an actual corrosion rate;

the improvement comprising the step of magnetically filtering ferric-ferrous oxides from said boiler water, prior to said step of obtaining a known aliquot volume of a boiler water sample.

4. The method of claim 3 wherein said acidic buffer solution is an acetate solution.

* * * * *

UNITED STATES PATENT AND TRADEMARK OFFICE
CERTIFICATE OF CORRECTION

PATENT NO.    : 5,898,002
DATED         : April 27, 1999
INVENTOR(S)   : Terrence P. Small It is certified that error appears in the above-identified patent and that said Letters Patent is hereby corrected as shown below:

On the title page, the inventors name should read
-- Terrence P. Small --

In Column 3, line 55, delete "ferrcous" and substitute therefor --- ferrous ---.

In Column 5, line 34, delete "75 ppm" and substitute therefor --- 5 ppm ---.

Signed and Sealed this

Sixteenth Day of November, 1999

Attest:

Attesting Officer

Q. TODD DICKINSON

Acting Commissioner of Patents and Trademarks